US012685453B2

(12) United States Patent (10) Patent No.: US 12,685,453 B2
Lai et al. (45) Date of Patent: Jul. 21, 2026

(54) SYSTEM AND METHOD FOR MONITORING BLOOD PERFUSION

(71) Applicant: KONINKLIJKE PHILIPS N.V., Eindhoven (NL)

(72) Inventors: Marco Lai, Eindhoven (NL); Claudio Dicorato, Milan (IT); Frank Verbakel, Helmond (NL); Gerhardus Wilhelmus Lucassen, Eindhoven (NL); Nico Maris Adriaan De Wild, Eindhoven (NL); Marc Godfriedus Marie Notten, Elsloo (NL)

(73) Assignee: Koninklijke Philips N.V., Eindhoven (NL)

( * ) Notice: Subject to any disclaimer, the term of this patent is extended or adjusted under 35 U.S.C. 154(b) by 145 days.

(21) Appl. No.: 18/266,354

(22) PCT Filed: Dec. 16, 2021

(86) PCT No.: PCT/EP2021/086166
§ 371 (c)(1),
(2) Date: Jun. 9, 2023

(87) PCT Pub. No.: WO2022/129319
PCT Pub. Date: Jun. 23, 2022

(65) Prior Publication Data
US 2024/0041342 A1 Feb. 8, 2024

(30) Foreign Application Priority Data

Dec. 17, 2020 (EP) ..................................... 20214955

(51) Int. Cl.
*A61B 5/026* (2006.01)
*A61B 5/024* (2006.01)

(52) U.S. Cl.
CPC ........ *A61B 5/0261* (2013.01); *A61B 5/02416* (2013.01)

(58) Field of Classification Search
CPC .......................... A61B 5/02416; A61B 5/0261
See application file for complete search history.

(56) References Cited

U.S. PATENT DOCUMENTS

| | | | | |
|---|---|---|---|---|
| 11,213,217 | B2 * | 1/2022 | Han ..................... | A61B 5/0295 |
| 2014/0163404 | A1 * | 6/2014 | Reichman ............ | A61B 5/0295 |
| | | | | 600/506 |

(Continued)

FOREIGN PATENT DOCUMENTS

| | | | | | |
|---|---|---|---|---|---|
| CN | 108186000 | A | * | 6/2018 | ......... A61B 5/02125 |
| CN | 111714105 | A | | 9/2020 | |

(Continued)

OTHER PUBLICATIONS

English Translation of CN-108186000-A (Year: 2018).*

(Continued)

*Primary Examiner* — Christopher Koharski
*Assistant Examiner* — Helene Bor

(57) ABSTRACT

An apparatus (and method) is for monitoring blood perfusion. A plurality of photoplethysmography, PPG, signals are acquired indicative of light detected in a region of interest of tissue at a plurality of respective locations within the region. The PPG signals are processed to determine an amplitude and preferably also a phase of each of the plurality of PPG signals, and a blood perfusion level is determined at the region of interest based on the amplitudes and preferably also the phases of the PPG signals.

12 Claims, 13 Drawing Sheets

Amplitude map

Phase map

(56)                    References Cited

U.S. PATENT DOCUMENTS

| | | | | |
|---|---|---|---|---|
| 2016/0022157 A1* | 1/2016 | Melker | ................ | A61B 5/7278 |
| | | | | 600/407 |
| 2017/0014087 A1 | 1/2017 | Verkruijsse | | |
| 2017/0079530 A1* | 3/2017 | DiMaio | ................ | A61B 5/0261 |
| 2023/0050190 A1 | 2/2023 | Buerger | | |
| 2024/0032819 A1* | 2/2024 | Zhao | .................... | A61B 5/1101 |

FOREIGN PATENT DOCUMENTS

| | | | | | | |
|---|---|---|---|---|---|---|
| WO | | 2016096591 | A1 | 6/2016 | | |
| WO | | 2017025775 | A1 | 2/2017 | | |
| WO | WO-2017121834 | A1 | * | 7/2017 | ........... | A61B 5/0033 |
| WO | | 2019003105 | A1 | 1/2019 | | |
| WO | WO-2020120543 | A1 | * | 6/2020 | ........... | A61B 5/0077 |

OTHER PUBLICATIONS

Bentham, Michael, Gerard Stansby, and John Allen. "Innovative multi-site photoplethysmography analysis for quantifying pulse amplitude and timing variability characteristics in peripheral arterial disease." Diseases 6.3 (2018): 81 (Year: 2018).*

International Search Report and Written Opinion of PCT/EP2021/086166, dated Mar. 23, 2022.
Staderini, Enrico M. et al "Near Infrared Device for Tissue Inflammation Evaluation", Materials Science Forum, vol. 879. Nov. 2016, pp. 2361-2364.
Shen, Hsuan et al "A Novel 500 Samples/Sec 4 by 4 Photoplethysmography (PPG) Array Based Cosmetic Chip Design", Computer Symposium (ICS) 2010, pp. 942-947.
Akovlev, Dmitry et al "Noncontact Blood Perfusion Mapping in Clinical Applications", Proceedings of the SPIE, vol. 9887, 2016.
https://www.mayoclinic.org/diseases-conditions/peripheral-artery-disease/symptoms-causes/syc-20350557, 2020.
https://www.hopkinsmedicine.org/health/treatment-tests-and-therapies/percutaneous-transluminal-angioplasty#procedure, 2020.
https://www.mayoclinic.org/tests-procedures/ankle-brachial-index/about/pac-20392934, 2022.
Briers, J David, Laser Doppler, Speckle and Related Techniques for Blood Perfusion Mapping and Imaging. Institute of Physics Publishing, Physiological Measurement, vol. 22 (4):R35, 2001.
Lai, Marco et al., "Perfusion Monitoring by Contactless Photoplethysmography (PPG) Imaging", Philips Research, 2016.

* cited by examiner

Amplitude map          Phase map

Amplitude MEDIAN

Amplitude MEDIAN

SYSTEM AND METHOD FOR MONITORING BLOOD PERFUSION

CROSS-REFERENCE TO PRIOR APPLICATIONS

This application is the U.S. National Phase application under 35 U.S.C. § 371 of International Application No. PCT/EP2021/086166, filed on Dec. 16, 2021, which claims the benefit of European Patent Application No. 20214955.5, filed on Dec. 17, 2020. These applications are hereby incorporated by reference herein.

FIELD OF THE INVENTION

This invention relates to the measurement of blood perfusion.

BACKGROUND OF THE INVENTION

Microcirculation is the circulation of the blood in the smallest blood vessels, present in the vasculature embedded within organ tissues. The purpose of microcirculation is to transport oxygen and nutrients to the tissue and remove the cell excreta.

The structure of the microvasculature is extremely complex, as so many capillaries are present in the tissues, with the individual capillaries so convoluted that the blood flow at any given point in any given capillary could be in any direction. For this reason, it can be stated that their overall function becomes averaged. That is, there is an average rate of blood flow through each tissue capillary bed, an average capillary pressure within the capillaries, and an average rate of transfer of substances between the blood of the capillaries and the surrounding interstitial fluid. This is the perfusion of the tissue.

Organ perfusion is a crucial indicator of injury and disease, which may include inflammation, stagnant or stopped blood flow, and all pathologies that can lead to global tissue hypoxia and organ dysfunction. Perfusion monitoring can be used to assess these microvascular injuries and many others, such as the progress of healing of either burned skin or wounds or the recovery of the perfusion downstream of a vessel lesion, and the necrosis (e.g., foot ulceration, sepsis) for patients with diabetes.

Among all these pathologies, there is also Peripheral Artery Disease, PAD (also called peripheral arterial disease). Peripheral artery disease is a common circulatory problem in which narrowed arteries reduce blood flow to the limbs. When a subject develops peripheral artery disease, the extremities, usually the legs, no longer receive sufficient blood flow to keep up with demand. This causes symptoms, most notably leg pain when walking (claudication). Peripheral artery disease is also likely to be a sign of a more widespread accumulation of fatty deposits in the arteries (atherosclerosis). This condition may reduce blood flow to the heart and brain, as well as the legs.

Peripheral artery disease can often be treated by quitting tobacco, exercising and eating a healthy diet. However, interventional treatments are also often needed. PAD pathologies are typically treated with Percutaneous Transluminal Angioplasty (PTA), in which a balloon inside the artery inflates at the site of a fatty clog to press it against the artery walls, which allows the blood to flow again. Percutaneous transluminal angioplasty, stenting and atherectomy are minimally invasive (endovascular) procedures that restore blood flow when arteries are clogged due to peripheral artery disease.

To assess the level of perfusion and hence to diagnose PAD, symptoms described by the patient may provide a first indication. A physician may also perform an ankle brachial index test (ABI). This test compares the systolic pressure at the arm with the systolic pressure reached in the two legs. Then an index R, which is the ratio between the pressure at the foot and the pressure at the arm, is computed. The ratio is then indicative of PAD:

R<0.4=Severe PAD
0.41<R<0.70=Medium severe PAD
0.71<R<0.90=Mild PAD
0.91<R<0.99=Borderline
1.00<R<1.29=No blockage The R index only gives an estimation of the severity of PAD and cannot be completely trusted by physicians. Since ABI involves the blockage of the blood flow, it cannot be used continuously during a procedure such as during PTA, but only after period of time (days or weeks) for assessing the improvement of the patient.

ABI devices thus cannot be used to assess in real-time, during any procedures, the effectiveness of a treatment. There are other technologies that can be used for perfusion monitoring. For example, a local perfused area can be analyzed using laser scattering technologies, for example, Laser Doppler Perfusion Imaging, or Laser Speckle Contrast Analysis. However, these technologies are costly, with limited motion robustness, and hard to commercialized with off the shelf components.

Another known monitoring system is imaging photoplethysmography (iPPG). This is a low cost, compact, non-contact sensing approach which gives real-time results and is much more motion robust with respect to other technologies, such as laser speckle. However, it has not demonstrate how PPG measurements may be used to determine a level of perfusion.

There remains a need for a low cost and non-invasive way to measure blood perfusion.

WO 2020/120543 discloses a remote PPG system for inflammation detection. Amplitude and phase maps are used to define, using a threshold method, if there is inflammation or not.

WO 2016/096591 discloses a method and system for allergy testing, by analyzing a skin response to a substance being tested, in particular using PPG pulse amplitudes.

SUMMARY OF THE INVENTION

The invention is defined by the claims.

According to examples in accordance with an aspect of the invention, there is provided an apparatus for monitoring blood perfusion, the apparatus comprising a processor configured to:

acquire, from at least one sensor, a plurality of photoplethysmography, PPG, signals indicative of light detected in a region of interest of tissue at a plurality of respective locations within the region of interest;

process the acquired plurality of PPG signals to determine at least an amplitude of each of the plurality of PPG signals; and determine a blood perfusion level at the region of interest based on at least the amplitudes of the PPG signals.

The invention enables a measure of perfusion to be derived from PPG signals, and these may for example be non-contact PPG signals obtained by a camera.

The processor is for example configured to process the acquired plurality of PPG signals to determine an amplitude and a phase of each of the plurality of PPG signals and determine a blood perfusion level at the region of interest based on the amplitudes and phases of the PPG signals.

The blood perfusion level is obtained based on amplitude information and preferably also phase information, such as amplitude and phase maps. It has been found that a higher amplitude corresponds to higher perfusion. Information about the distribution of the phase is also of particular interest, such as a standard deviation or interquartile range of the phase map. Areas which are well perfused are found to have a very similar phase (hence low variability) and good PPG amplitude, since blood flow arrives uniformly in the whole area. Areas not well perfused are found to have low PPG amplitude and more random phase, since the PPG signals are low and less coherent in the same small area. Therefore, the perfusion is correlated with the PPG amplitude and inversely correlated with the distribution of the phase.

The processor is for example configured to:
  determine a first value relating to an average of the determined amplitude value for the locations within the region of interest; and
  determine a second value relating to a distribution of the phase values for the locations within the region of interest.

For each pixel, an amplitude average may be obtained from the sensing performed over time and a measure of phase is obtained from the sensing performed over time. Thus, each location has one value of amplitude and one value of phase derived from the overall time period. Then, the first value is defined as e.g. a median or mean value of the amplitude of all locations (i.e. all pixels) and second value is a distribution of the phase of all locations (i.e. all pixels).

The number of locations, i.e. pixels, will depend on the resolution of the camera used and how large is the area of interest in the field of view. There are typically thousands of locations.

To provide the perfusion information, an amplitude map and a phase map may be displayed. To provide an actual representative value of the level of perfusion, the information is combined to generate an overall value (based on the first value, i.e. an average for the amplitude across the region of interest and the second value i.e. a distribution of the phase across the region of interest).

Each individual PPG signal (i.e. for a single location) is based on the change in brightness of a single pixel during the entire video. From these PPG signals (which are for spatially spread locations across the 2D region of interest), the amplitude map and phase image may be derived. The average is obtained by averaging the amplitude map (e.g. using a median or mean), while the phase distribution is computed using a distribution measure (e.g. a standard deviation or variance or interquartile range of the phase map).

The video frame rate is for example between 10 and 50 frames per second and the video duration is for example 5 to 30 seconds. Different frame rates and durations could however be used.

The first value characterizes the PPG amplitude (for the combination of the pixels) and the second value characterizes the PPG phase distribution (across all pixels), and these both correlate to the perfusion level as explained above.

Thus, by taking both of these values into account, an accurate perfusion level can be derived at a particular pixel, i.e. at a particular location.

The processor may be configured to determine a blood perfusion level using a ratio between the first value and the second value. The perfusion is proportional to the amplitude A, and inversely proportional to the distribution of the phase P. Thus, the ratio of the first and second values is representative of the perfusion.

The first value is for example a median or mean of the amplitudes for the locations. The second value is for example an interquartile range or standard deviation of the phase for the locations.

The first value (median or mean of the amplitude) and the second value (distribution of the phase) are thus derived from the whole region of interest, but possibly also from a portion of the overall imaged region. However, in that case, the "region of interest" may be considered to be only that portion of the image for which the first and second values are being calculated. In each pixel of the amplitude map (corresponding to a skin location) there is a single value of amplitude, and in each pixel of the phase map there is a single value of phase.

The processor may be configured to determine the blood perfusion at the region of interest as a value relative to the blood perfusion for the region of interest at a previous time. Thus changes over time are then considered of interest.

The processor may be further configured to:
  acquire from at least one further sensor a plurality of photoplethysmography, PPG, signals indicative of light detected in a reference region and to determine a blood perfusion level for the reference region; and
  determine the blood perfusion at the region of interest as a value relative to the blood perfusion for the reference region.

Thus, perfusion levels relative to other parts of the body may be considered of interest.

The at least one sensor is for example a non-contact PPG sensor.

The invention also provides a method for monitoring blood perfusion, comprising:
  acquiring, from at least one sensor, a plurality of photoplethysmography, PPG, signals indicative of light detected in a region of interest of tissue at a plurality of respective locations within the region;
  processing the acquired plurality of PPG signals to determine at least an amplitude of each of the plurality of PPG signals; and
  determining a blood perfusion level at the region of interest based on at least the amplitudes of the PPG signals.

The method may comprise:
  processing the acquired plurality of PPG signals to determine an amplitude and a phase of each of the plurality of PPG signals:
  determining a first value relating to an average of the determined amplitude value for the locations; and
  determining a second value relating to a distribution of the phase values for the locations.

The method may then comprise determining a blood perfusion level at the location using a ratio between the first value and the second value.

The first value may be a median or mean of the amplitudes for the locations and the second value may be an interquartile range or standard deviation of the phase for the locations.

5                                                                                      6

The method may comprise:

determining the blood perfusion at the region of interest as a value relative to the blood perfusion for the region of interest at a previous time; or determining the blood perfusion at the region of interest as a value relative to the blood perfusion for a reference region.

The invention also provides a computer program comprising computer program code means which is adapted, when said program is run on a computer, to implement the method of defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
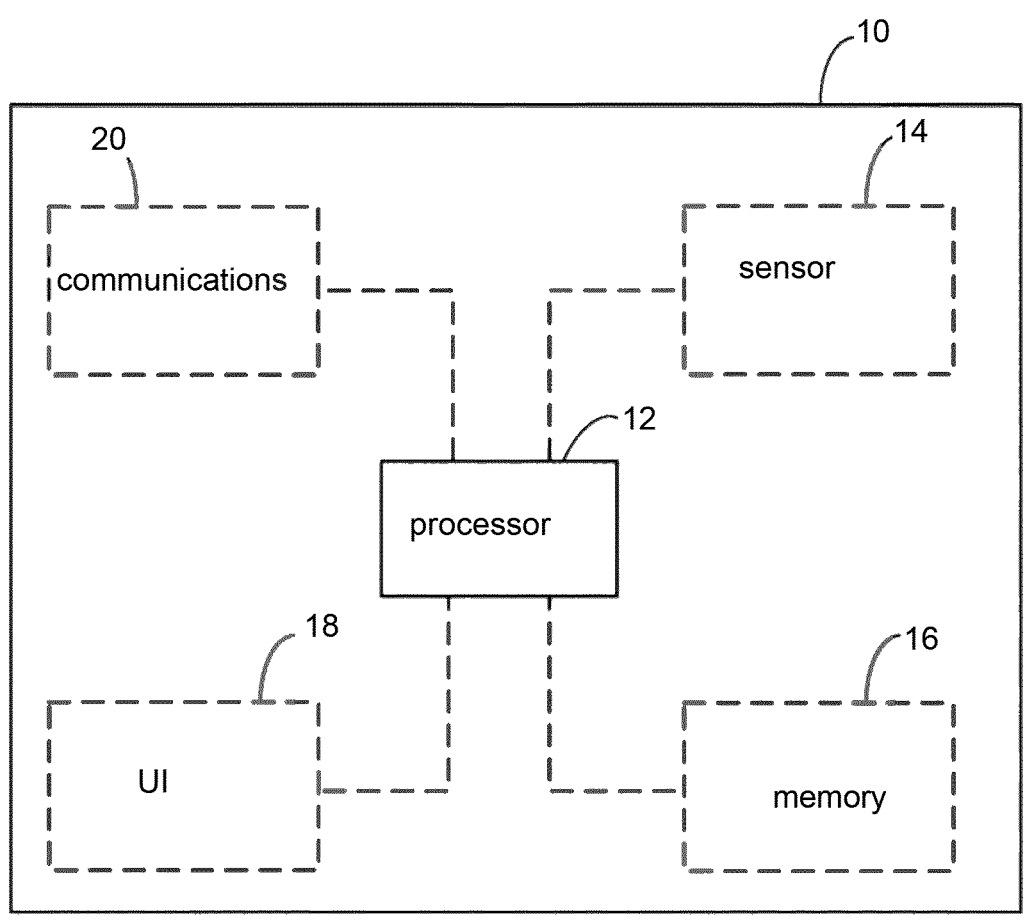
FIG. 1 shows an example of a system for monitoring perfusion.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an apparatus (and method) for monitoring blood perfusion. A plurality of photoplethysmography, PPG, signals are acquired indicative of light detected in a region of interest of tissue at a plurality of respective locations within the region of interest. The PPG signals are processed to determine an amplitude and preferably also a phase of each of the plurality of PPG signals, and a blood perfusion level is determined at the region of interest based on the amplitudes and preferably also the phases of the PPG signals.

The system comprises a camera or series of cameras (at one or multiple wavelengths) for recording images of the skin area as video sequences, preferably at a distance. The measurements derived from the video sequences are the remote photoplethysmography (PPG) signals, which provide non-contact measurement of pulse signals by analyzing subtle changes of skin color at certain wavelengths of the light.

FIG. 1 shows an example of a system 10 for monitoring perfusion. The apparatus comprises a processor 12, a sensor 14, a memory 16, a user interface 18 and communications circuitry 110.

The processor 12 is configured to acquire a plurality of photoplethysmography (PPG) signals indicative of light detected in a region of interest of tissue at a plurality of respective locations within the region. The region of tissue referred to herein may also be referred to as a region of interest (ROI) of the tissue. The processor 12 is configured to acquire the plurality of PPG signals from the at least one sensor 14. The processor 102 is also configured to process the acquired plurality of PPG signals to determine an amplitude and a phase of each of the plurality of PPG signals.

The processor 12 is configured to determine a level of perfusion based on the determined amplitude and phase of each of the plurality of PPG signals as explained further below.

The at least one sensor 14 is configured to obtain the plurality of PPG signals from the region of interest of the tissue, at the plurality of respective locations within the region. The sensor may an in internal part of the system or it may be remote from the other components. The sensor may be configured to obtain the plurality of PPG signals at a single (e.g. a certain) wavelength of light or it may perform measurements at a plurality of wavelengths. The sensor 14 may be a single sensor or a plurality (e.g. a series) of sensors. The sensor is for example a pulse oximeter configured to illuminate the region of tissue and measure changes in light absorption within the region of tissue to acquire the plurality of PPG signals. The sensor may instead be a camera which can be configured to measure changes in tissue color to acquire the plurality of PPG signals, or any other sensor or combination of sensors suitable for obtaining PPG signals. The sensor may be positioned at distance from (e.g. remote from) the tissue. Thus, the at least one sensor 14 is preferably a non-contact PPG sensor capturing non-contact PPG signals.

However, in some examples the at least one sensor 14 may be positioned such that it contacts the tissue to obtain the plurality of PPG signals.

By way of example, the frame rate of the capture images is 25 frames per second, and a video duration of 15 seconds may be used, giving 375 PPG samples at each pixel of the PPG sensor, i.e. the camera in the preferred example.

Motion stabilization may be used, such as the Kanade-Lucas-Tomasi (KLT) algorithm, for compensating human motion, such that the region of interest (ROI) is stabilized and each pixel always corresponds to the same skin location. Subsequent extraction of the PPG signal may be achieved with low-pass filtering of each video frame by convolution with a square kernel of 5×5 pixels, to increase the signal-to-noise-ratio (SNR). The pulsatile component (AC) of the PPG signal may be normalized with respect to its baseline component (DC), so expressing the amplitude of the PPG signal as a percentage, as expressed by the equation:

$$PPG_{norm} = \frac{PPG_{AC}}{PPG_{DC}} - 1$$

This compensates for the parameters that affect both AC and DC signal components, such as intensity of the incident light or skin tone of the subject. The baseline DC component comprises frequencies up to 0.5 Hz, while the pulsatile AC component comprises frequencies within the range 0.5-10 Hz.

The memory 16 may be internal to the system or it may for example be pat of a hospital database, or it may be part of a cloud computing resource, or similar. The memory 16 may comprise any type of non-transitory machine-readable medium, such as cache or system memory including volatile and non-volatile computer memory such as random access memory (RAM), static RAM (SRAM), dynamic RAM (DRAM), read-only memory (ROM), programmable ROM (PROM), erasable PROM (EPROM), and electrically erasable PROM (EEPROM). The memory 16 for example also stores program code that can be executed by the processor 12. The memory 16 may also be configured to store information required by or resulting from the monitoring method.

The memory 16 for example is configured to store any one or more of the acquired plurality of PPG signals, the determined amplitude of one or more of the plurality of PPG signals, the determined phase of one or more of the plurality of PPG signals, and the determined tissue perfusion level.

The user interface 18 can be configured to render (or output or display) information required by or resulting from the processing method. For example, the user interface 18 may be configured to render one or more of the acquired plurality of PPG signals, the determined amplitude of one or more of the plurality of PPG signals, the determined phase of one or more of the plurality of PPG signals, the determined perfusion level, or any other information. The user interface 18 may also receive a user input. It for example comprises one or more of buttons, a keypad, a keyboard, a mouse, a touch screen or an application (for example, on a smart device such as a tablet, a smartphone, or any other smart device), a display or display screen, a graphical user interface (GUI), one or more speakers, one or more microphones or any other audio component, one or more lights (such as light emitting diode LED lights), a component for providing tactile or haptic feedback (such as a vibration function, or any other tactile feedback component), an augmented reality device (such as augmented reality glasses, or any other augmented reality device), a smart device (such as a smart mirror, a tablet, a smart phone, a smart watch, or any other smart device), or any other user interface, or combination of user interfaces.

The communications interface 120 is for enabling the apparatus, or components of the apparatus, to communicate with and/or connect to one or more other components (e.g. one or more sensors, interfaces, devices, processors, or memories). The communications interface 20 may enable the apparatus 10, or components of the apparatus 100, to communicate and/or connect wirelessly, via a wired connection, or via any other communication (or data transfer) mechanism.

Figure 2:
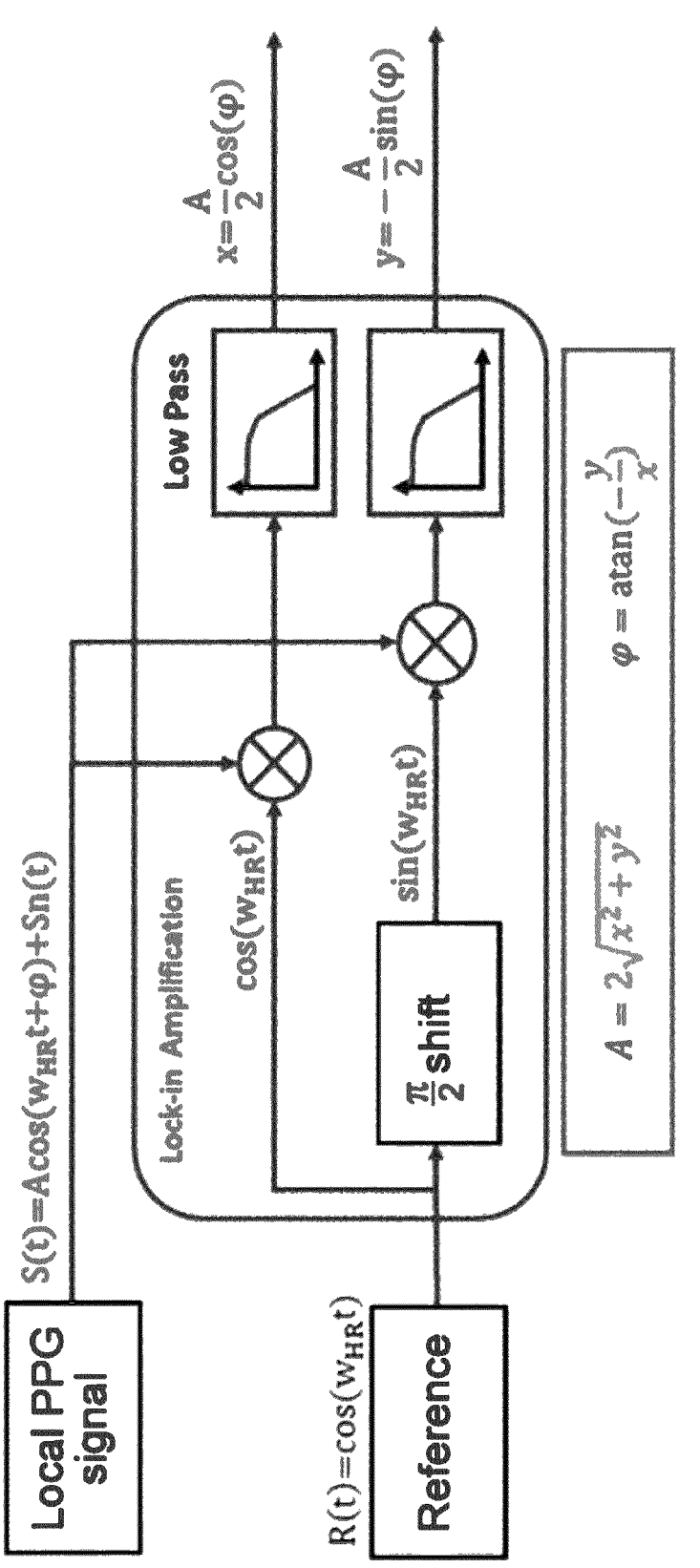
FIG. 2 shows camera images are processed.

FIG. 2 shows how the camera images are processed. It involves generation of a PPG amplitude map and a PPG phase map. WO 2020/120543 discloses a remote PPG system for inflammation detection, and the processing system of FIG. 2 is discussed in WO 2020/120543. In WO 2020/120543, the amplitude and phase maps are used to define, using a threshold method, if there is inflammation or not. The phase may be considered as a delay in time for the blood flow to arrive in the area. This delay depends on the properties of the vessels (resistance and compliance). Inflamed tissue differs from non-inflamed both because its amplitude in the PPG map is higher, but also because there is a different delay for the blood flow to arrive (difference in resistance and compliance).

This invention instead relates to the determination of a perfusion level and is based on the realization that the information obtained by the processing, explained below, of FIG. 2 may also be used to derive a perfusion level. In particular, it has been found that a higher amplitude corresponds to higher perfusion. Information about the distribution of the phase is used, such as a standard deviation of the phase map. It has been found that areas which are well perfused have a very similar phase (low standard deviation) and good PPG amplitude, since blood flow arrives uniformly in the whole area. Areas not well perfused have low PPG amplitude and more random phase, since the PPG signals are low and less coherent in the same small area. Therefore, the perfusion is correlated with the PPG amplitude and inversely correlated with the distribution of the phase.

The processing system of FIG. 2 determines the amplitude and phase shift of each of a plurality of PPG signals, in particular for each pixel (i.e. for each skin location) of the camera image capturing an image of a region of interest. The phase is representative of a pulse arrival time and the phase shift indicates a relative pulse arrival time to a respective location (relative to a reference PPG signal in common with the entire region of interest). The particular example shown uses lock-in amplification, but any other known methods for computing amplitude and phase may be employed.

A plurality of PPG signals is obtained, each indicative of light detected in a region of tissue at a respective locations within the region of interest. The plurality of PPG signals can be referred to as a plurality of "local" PPG signals. As illustrated in FIG. 2, the input to the method is a reference signal R(t) and a local PPG signal S(t). The reference signal R(t) can be expressed as:

$$R(t)=\cos(w_{HR}t)$$

The value $w_{HR}$ is a heart rate frequency and t is time. The reference signal R(t) is thus a cosine modulated at the heart rate frequency, which is defined as the modulating frequency of the PPG signal determined by averaging the data from all the pixels of the region of interest (ROI) recorded.

The local PPG signal S(t) (i.e. for a single pixel of the camera and hence a single skin location) can be expressed as:

$$S(t)=A\ \cos(w_{HR}t+\varphi)+Sn(t)$$

A is the amplitude of the modulating heart rate frequency $w_{HR}$, $\varphi$ is the phase shift of the local PPG signal S(t) with respect to the reference signal R(t), Sn(t) contains all the other frequency components, and t is time.

The signal S(t) is the local PPG signal extracted from a single pixel, with amplitude A of the modulating heart rate frequency, and $\varphi$ the phase shift of the signal S(t) with respect to R(t).

R(t) and S(t) are fed into the lock-in amplification block and S(t) is multiplied by R(t), namely by $\cos(w_{HR}t)$, and R(t) is phase shifted by 90 degrees, namely to $\sin(w_{HR}t)$. The signal S(t) is thereby multiplied by R(t) and the sine form of R(t).

The two output signals of these operations are then low-pass filtered. The low-pass filtering may, for example, be performed by averaging the two output signals over time, but it will be understood that any other form of low-pass filtering may instead be used.

Thus, for each pixel, an amplitude average is obtained from the sensing performed over time and a measure of phase is obtained from the sensing performed over time. Thus, each location has one value of amplitude and one value of phase derived from the overall sensing time period. This involves a first average process.

As a result of the low pass filtering, two values x and y are obtained as:

$$x=A/2\ \cos(\varphi)$$

$$y=-A/2\ \sin(\varphi)$$

These are the real and imaginary parts of the steady complex signal which is the product of R(t) and S(t), averaged over time.

Thus, by averaging R(t) and S(t) over time, x and y are obtained, which are correlated to the amplitude A of the local PPG signal and to the phase shift $\varphi$ of the local PPG signal with respect to R(t). By combining the values x and y, the amplitude A of the local PPG signal and the phase shift $\varphi$ of the local PPG signal can be expressed as follows:

$$A=2\sqrt{x^2+y^2}$$

$$\varphi=a\ \tan(-x/y)$$

Thus, for each of the plurality of PPG signals, a single value that represents the amplitude of the PPG signal for the overall sensing time and a single value that represents the phase shift of the PPG signal for the overall sensing time can be determined.

In this way, by extracting pulse signals at each individual location of the skin region, a spatial map of the pulse signal, e.g., amplitude and phase, can be derived.

The perfusion represented by the obtained amplitude map may then be color coded, for example with blue indicating low perfusion and red indicating high perfusion.

By extracting $\varphi$ from the PPG signal of each pixel of the video sequence, a PPG phase map is also obtained. The perfusion of the obtained PPG phase map may also be color coded, with values ranging from −180 to +180 degrees. The phase represents the delay in time of the PPG signal wave at that location, with respect to a reference PPG signal in common with the entire region of interest.

Figure 3:
FIG. 3 shows an amplitude map on the left and a phase map on the right.
Figure 3:
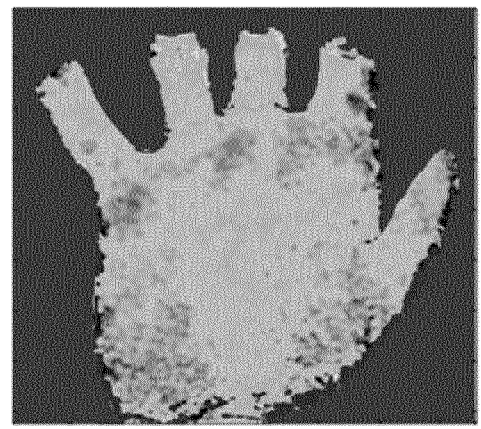

FIG. 3 shows an amplitude map on the left and a phase map on the right. In practice, and the grey levels shown represent different colors.

Figure 4:
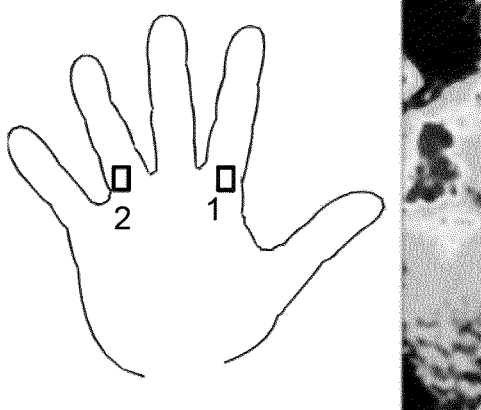
FIG. 4 shows a representation of a hand with two monitoring locations, and amplitude map and a phase map processed from the hand images.
Figure 4:
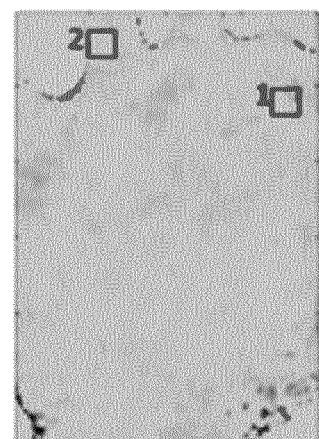

FIG. 4 shows in the left a representation of a hand with two monitoring locations labeled 1 and 2. The middle top image shows an amplitude map and the top right image shows a phase map processed from the hand.

Figure 5:
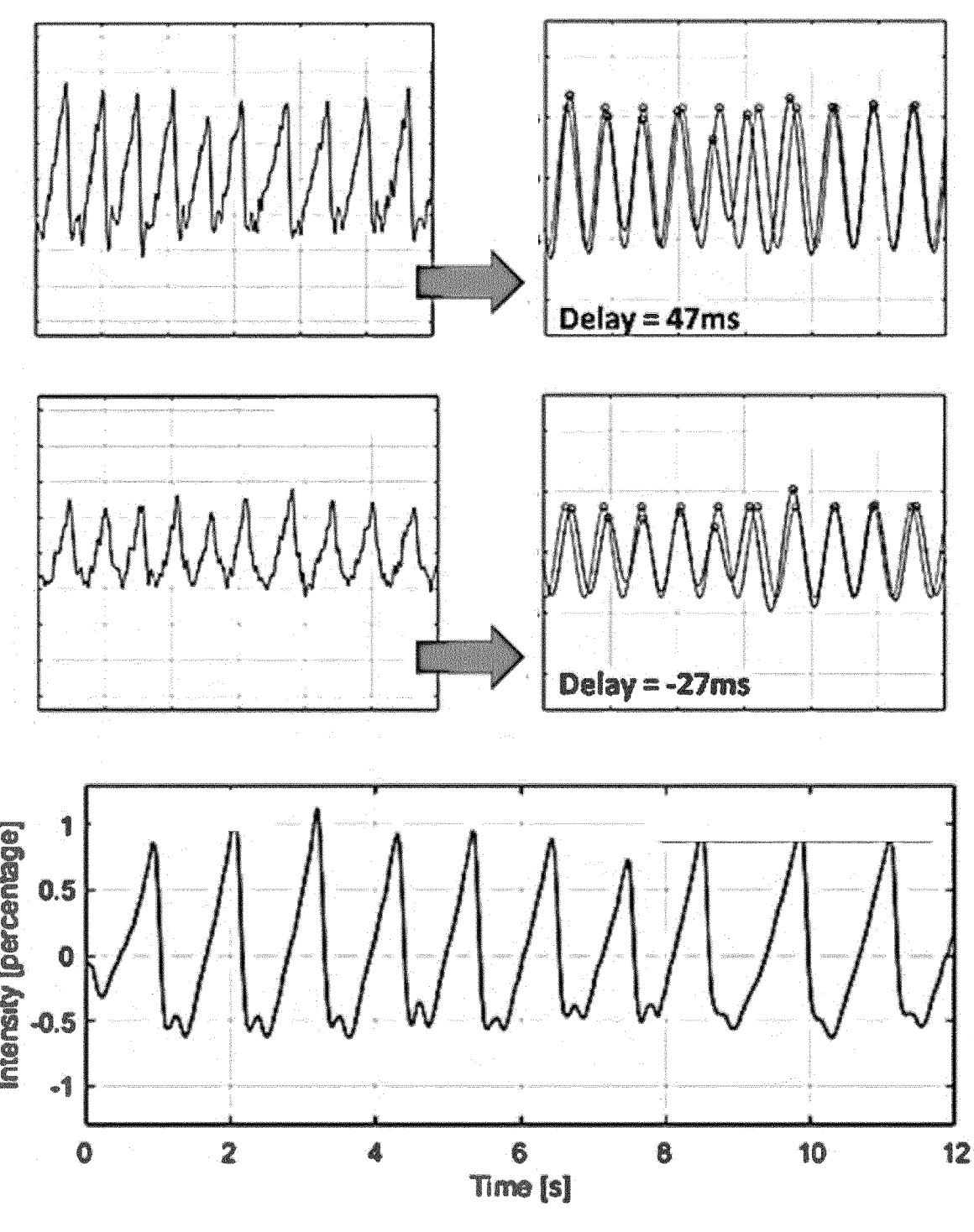
FIG. 5 shows local PPG signals extracted from the two numbered areas of FIG. 4 as well as a reference signal extracted from the whole region of interest.

FIG. 5 shows local PPG signals extracted from the two numbered areas on the hand image. The top images of FIG. 5 show the local PPG signal from location 1 and the middle images of FIG. 5 shows the local PPG signal from location 2.

The bottom of FIG. 5 shows a reference PPG signal obtained as an average PPG intensity of the entire region of interest is shown. This reference signal is used to obtain a heart rate and in order to extract the perfusion map. This reference signal is filtered and the heart rate frequency is extracted. In this case, the subject has a heart rate of 52 bpm (young volunteer, 25 years old).

In the top and middle images, the left plot is the raw PPG signal from the location of interest. The right plot shows a filtered version of the raw PPG signal and also a filtered version of the reference signal. The signals are all filtered around the heart rate frequency, with the result that they are more clean sinewaves.

The amplitude of the local PPG signal does not have the same strength over the entire hand. Indeed, a perfusion map may be built by color coding the amplitude of the PPG signal in each area as mentioned above.

Furthermore, the right images show that peaks of the local PPG signals and the peaks of the reference do not always match. This can be considered as a delay. The average delay is shown in the right images. If the delay is positive, the reference signal arrives slightly before the local signal. If the delay is negative, the reference signal arrives later than the signal. By color coding the delay on the hand, a color coded phase map is also obtained. The phase map is coded in degrees, in that the delay (in seconds) is coded as a fraction of the heart rate cycle period. The phase map value can easily be converted to a time delay value:

$$\text{Delay} = \frac{\varphi}{360} * \frac{1}{\text{Heart rate}} = \frac{\varphi}{360} * \text{Heart rate period}$$

The sensitivity of the system has been tested in detecting perfusion changes, by inducing a perturbation in the skin perfusion of several volunteers.

Figure 6:
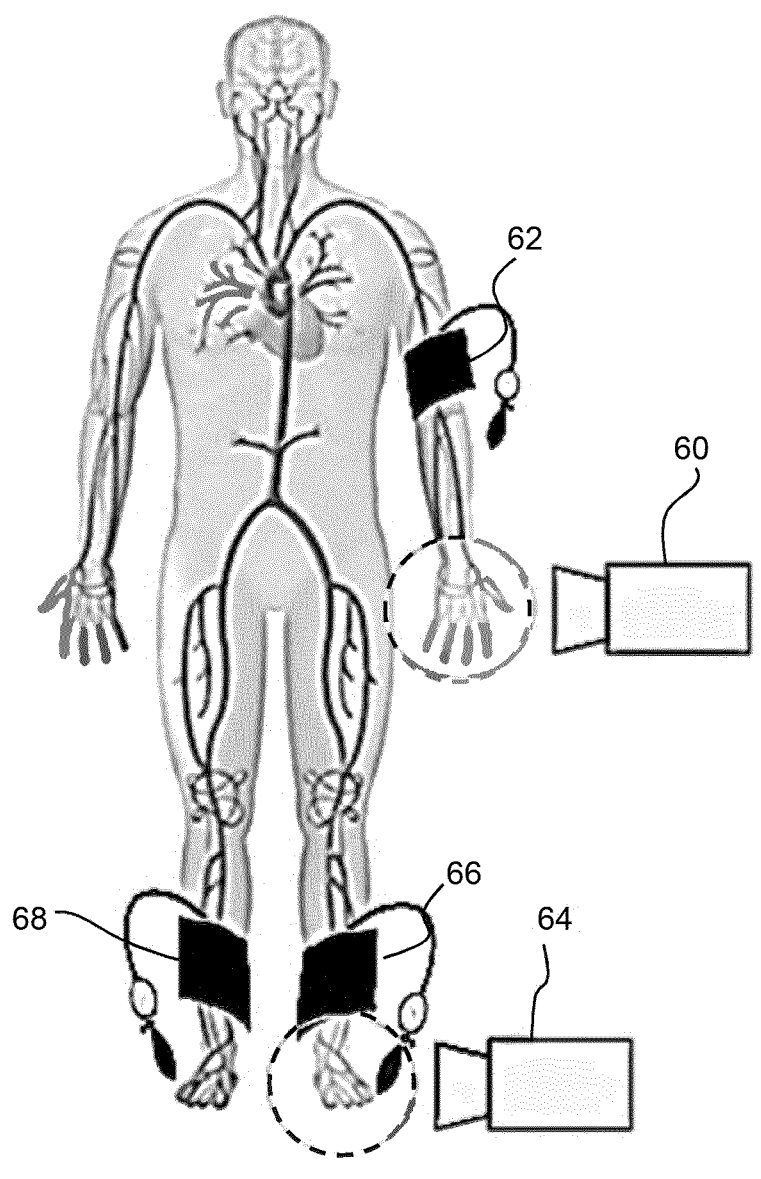
FIG. 6 shows the set up of an experimental system for demonstrating the feasibility of the invention.

FIG. 6 shows the set up of the system.

For monitoring perfusion at the hand, a camera system 60 is provided taking image of the hand, and to provide control of the perfusion level, a pressure cuff 62 is provided above the elbow.

For monitoring perfusion at the foot, a camera system 64 is provided taking image of the foot, and to provide control of the perfusion level, a pressure cuff 66 is provided above the ankle.

A pressure cuff 68 is provided above the other ankle. This enables an ABI test to be performed. The ABI test compares the systolic pressure at the level of both ankles with the perfusion level at the level of the arm. In this particular test, an ABI system was used formed by three cuffs, one 62 at the arm and two 66,68 at the legs. The perfusion at the hand was compared with the perfusion at the left leg by using cameras 60 and 64.

In a real implementation, rather than the test configuration of FIG. 6, there is no need for the pressure cuffs.

It has been observed that the perfusion of the skin is directly correlated to the amplitude map and inversely correlated to the distribution of the phase map.

Using the setup show in FIG. 6, five experiments on different subjects were conducted, recording the perfusion on the hand and foot with:

(i) no pressure applied on the arm (for the hand monitoring) or leg (for the foot monitoring) to provide a baseline.

(ii) with 40% of the systolic pressure applied on the arm (or leg), then with 80%, then with 120% and eventually with a deflated cuff condition to represented perfusion after flow restoration.

The 120% measurement may be considered as pressure completely blocked.

Amplitude and phase maps were obtained for the five measured conditions. By observing the images, it was found that the perfusion level displayed in the amplitude map decreases as more pressure is applied on the arm. Instead in the phase map, as the perfusion decreases, a more noisy distribution of the phase was observed.

Below are presented several examples of perfusion, acquired on volunteers, obtained by applying an external pressure around the arm and leg of the subject.

Figure 7:
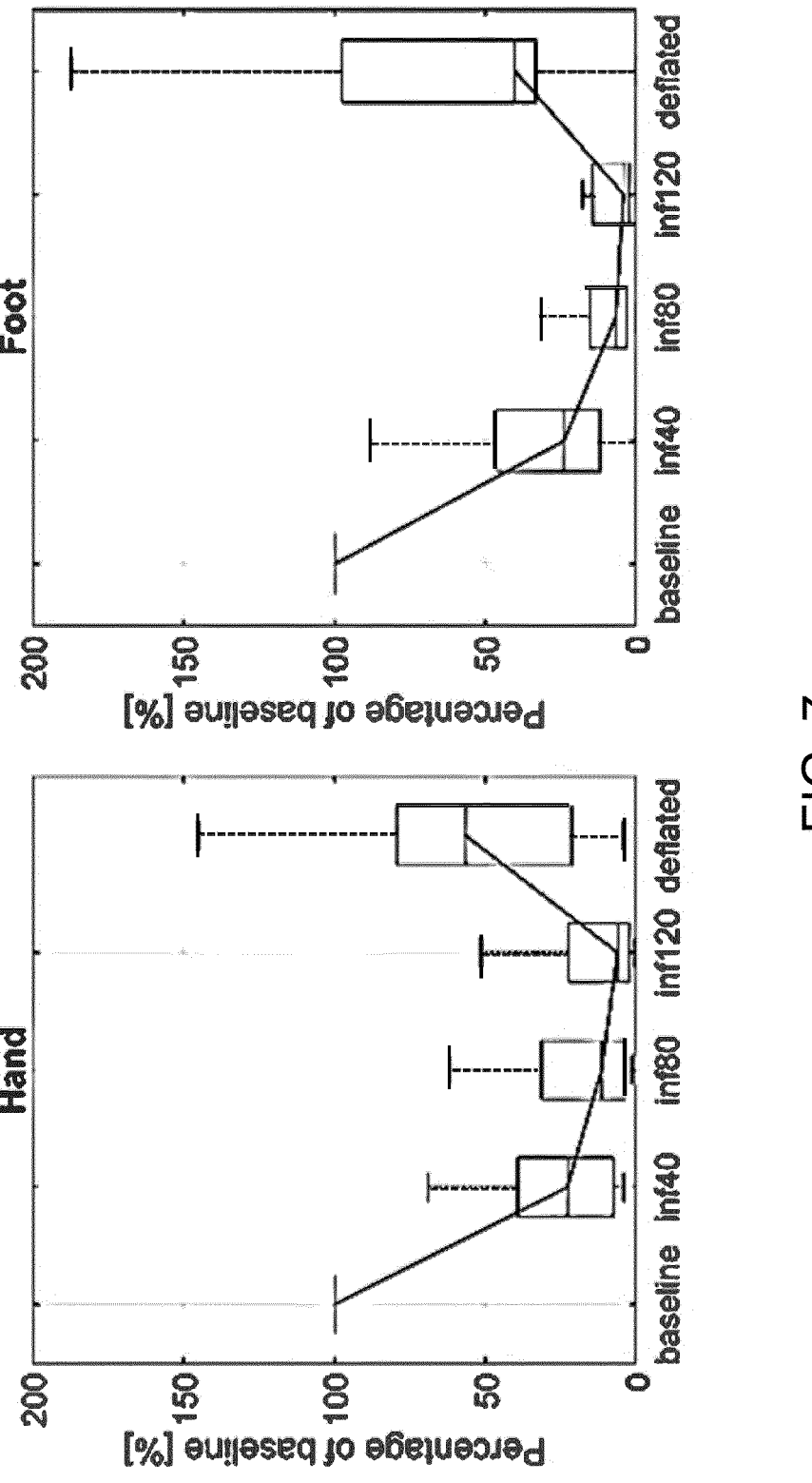
FIG. 7 shows boxplots representing the different distributions of the amplitude of the PPG signal recorded on the hand and foot for the baseline (no cuff), 40%, 80% and 120% of systolic cuff pressures, and deflated cuff.

FIG. 7 shows the different distributions of the amplitude of the PPG signal recorded on the hand (left image) and foot (right image) at the different pressure levels applied to the arm and leg respectively. The plots are box plots showing the mean value for the different volunteers as well as the interquartile range of values for the different volunteers. The lower bar of the box thus represents the first quartile, and the upper bar of the box represents the third quartile. The interquartile range is the range between the first and the third quartiles.

The boxplots in this test are populated with measures taken on 21 volunteers. Each point of the boxplot is a median value of the amplitude map taken on a volunteer. For each volunteer, 2 measures were taken.

It can be seen that the measured perfusion goes down as the pressure applied at the limb increases. During the deflating measure, perfusion does not go back completely to normal. In the experiments conducted, a delay of 3 minutes was used after the 120% measurement before taking the deflated measure. A longer time delay would have resulted in the perfusion reaching closer to the initial value.

Figure 8:
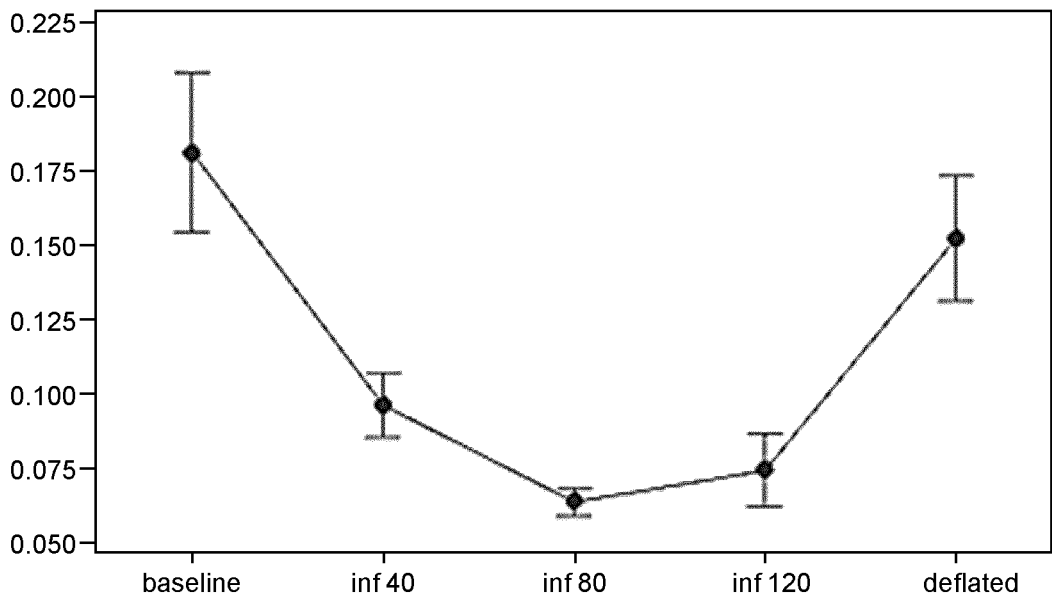
FIG. 8 shows an analysis of variance (ANOVA) for the median of the amplitude and phase of the PPG signal for no cuff, 40%, 80% and 120% of systolic cuff pressures, and deflated cuff with the 95% confidence interval showing.
Figure 8:
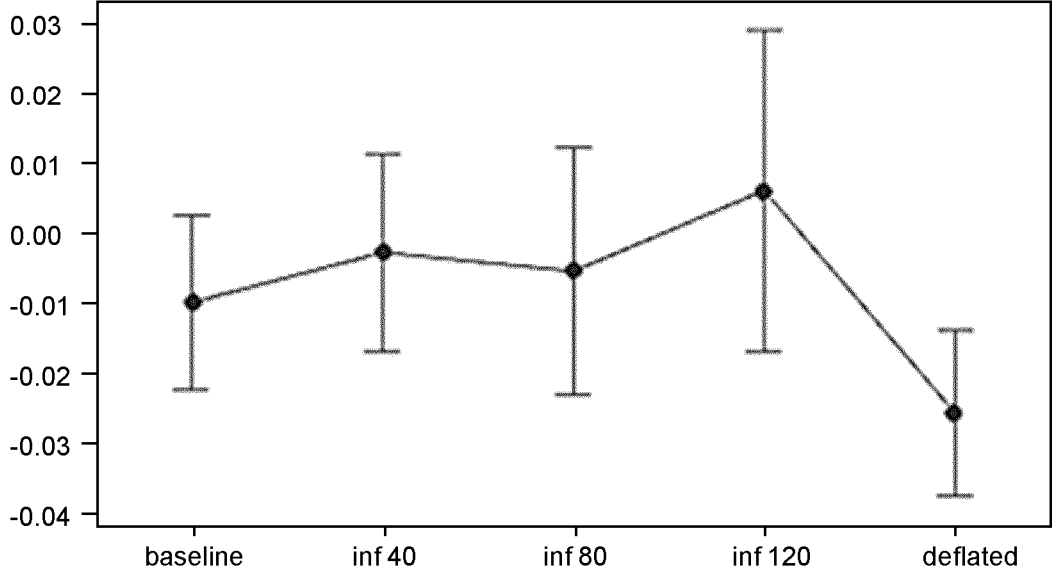
Figure 9:
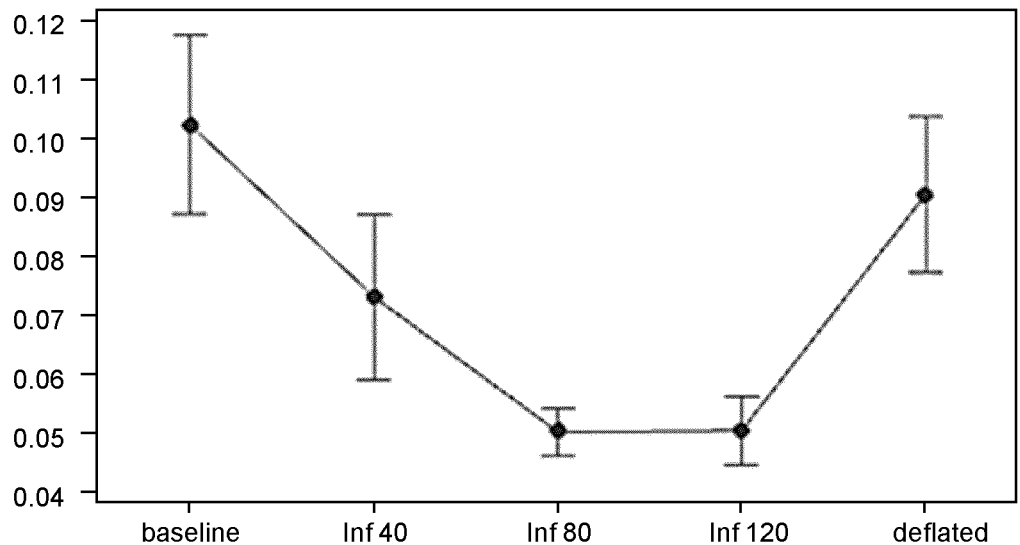
FIG. 9 an analysis of variance (ANOVA) for the IQR of the amplitude and phase of the PPG signal for no cuff, 40%, 80% and 120% of systolic cuff pressures, and deflated cuff with the 95% confidence interval showing.
Figure 9:
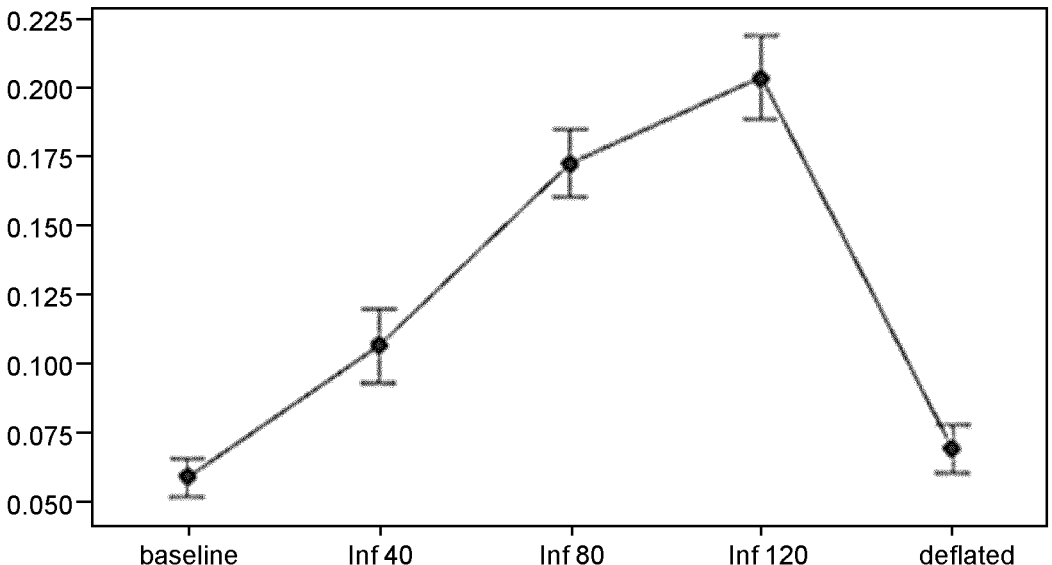

FIGS. 8 and 9 show an analysis of variance (ANOVA) of the main components of the PPG signal for the foot obtained from 25 volunteers. Each point represents a mean value and the distance to the bars are 95% confidence intervals.

The top image of FIG. 8 shows a plot of the median and variance of the amplitude map at the different cuff pressures (baseline, 40% inflation, 80% inflation, 120% inflation, and deflated).

The bottom image of FIG. 8 shows the median and variance of the phase map at the different cuff pressures.

The top image of FIG. 9 shows a plot of the interquartile range (IQR) of the amplitude map at the different cuff pressures. The bottom image of FIG. 9 shows the IQR of the phase map at the different cuff pressures. The intervals are again based on individual standard deviations.

FIGS. 8 and 9 show that it is possible to distinguish between (most of) the cuff pressure levels in the amplitude and phase components. Despite the good correlation, the IQR of the phase map is not preferred as the primary predictor for perfusion level as it is not sensitive to a loss of total PPG signal.

Figure 10:
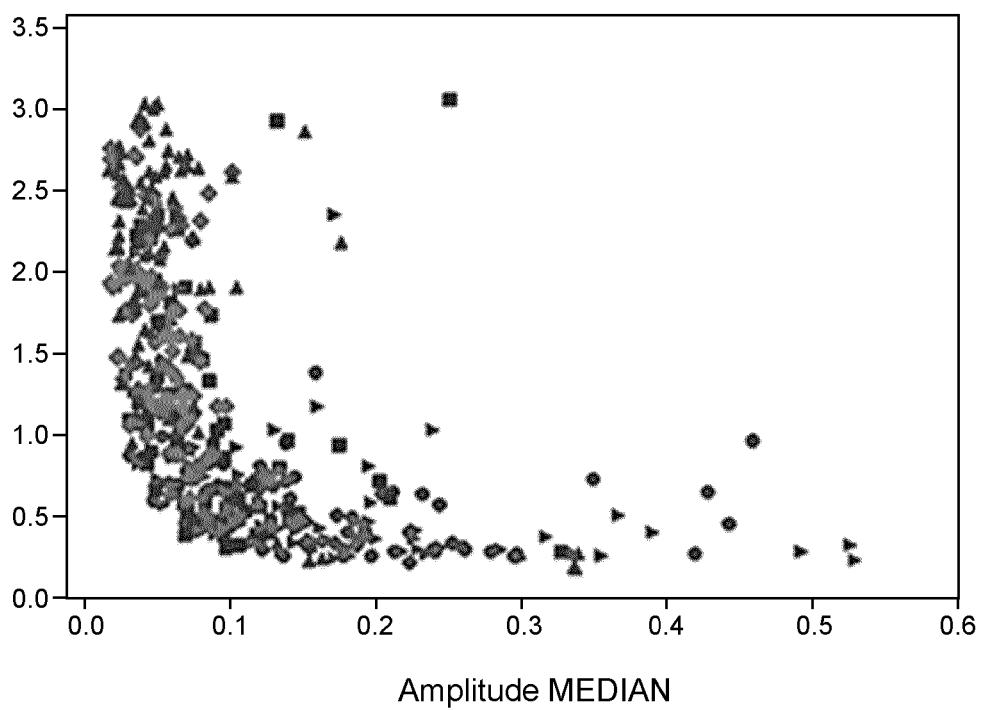
FIG. 10 shows scatterplots of the interquartile range of the phase map versus the median of the amplitude of the foot.
Figure 10:
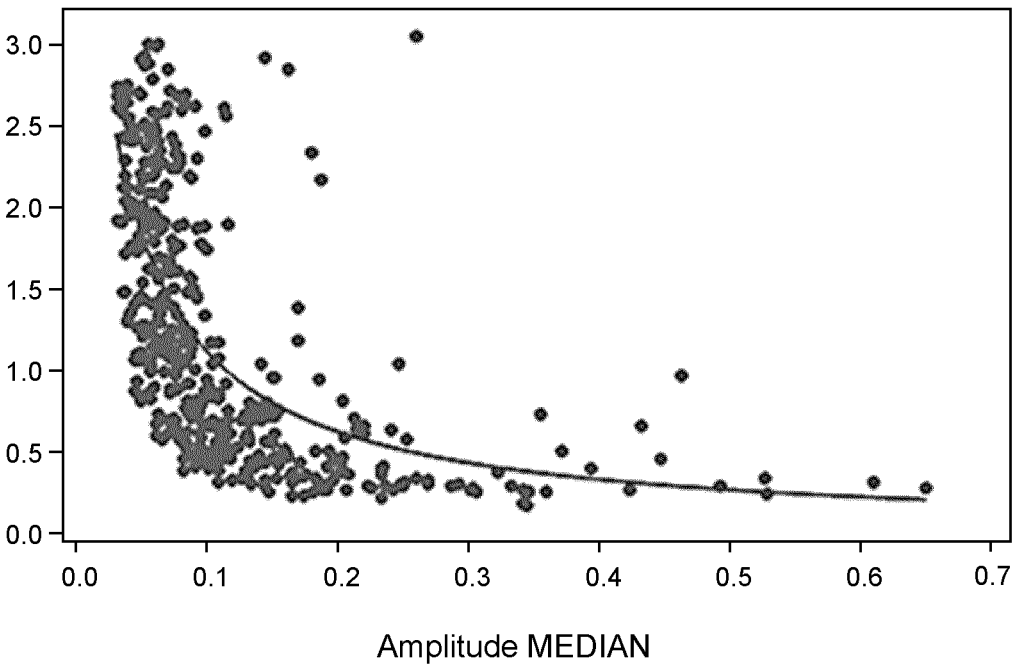
Figure 11:
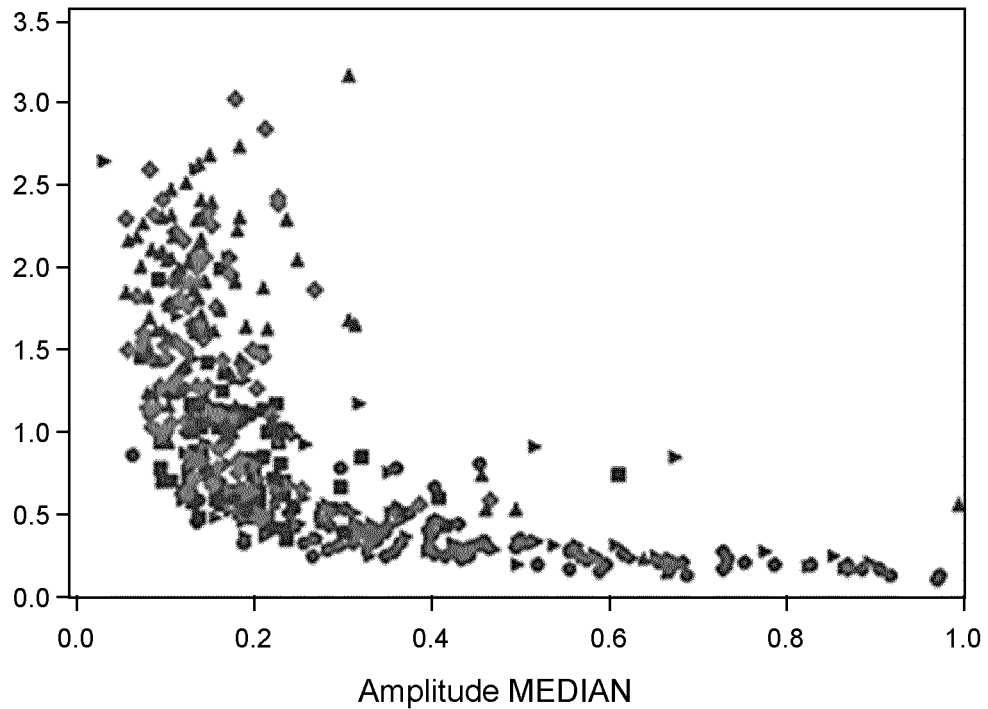
FIG. 11 shows scatterplots of the interquartile range of the phase map versus the median of the amplitude of the hand.
Figure 11:
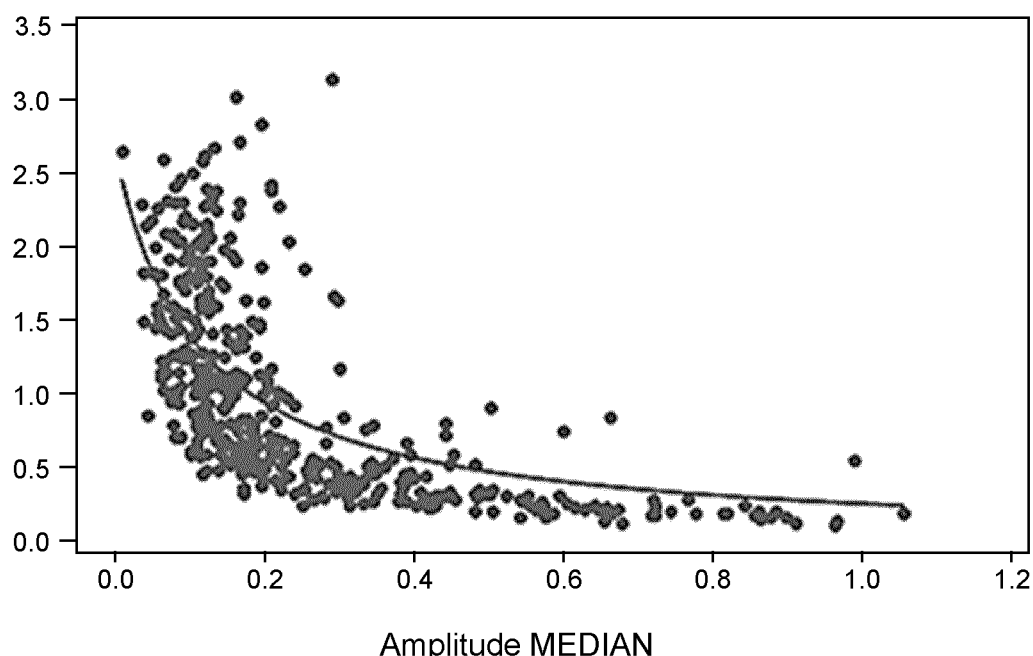

FIGS. 10 and 11 show scatterplots of the IQR of the phase map versus the median of the amplitude.

In this test, there are 21 subjects and 5 pressure levels, and two measurements per subject. This gives 220 scatter points, each scatter point representing one measurement of IQR for the overall region of interest.

The top image of FIG. 10 shows a scatter plot, with two points for each subject and for each cuff pressure level for the foot experiment. The bottom image shows a fitted line (with a function y=1/(ax+b)) to the scatter plot.

The top image of FIG. 11 shows a scatter plot, again with two points for each subject and for each cuff pressure level for the hand experiment. The bottom image shows a fitted line to the scatter plot (again with a function y=1/(ax+b)).

FIGS. 10 and 11 show a correlation between the IQR of the phase map and the median of the amplitude map. The distribution follows a 1/x regression line. The points of the baseline group are on the bottom of the curve (hence with high phase coherence and high amplitude) and the 120% pressure level results are located at the top of the curve (hence with low phase coherence and low amplitude).

Figure 12:
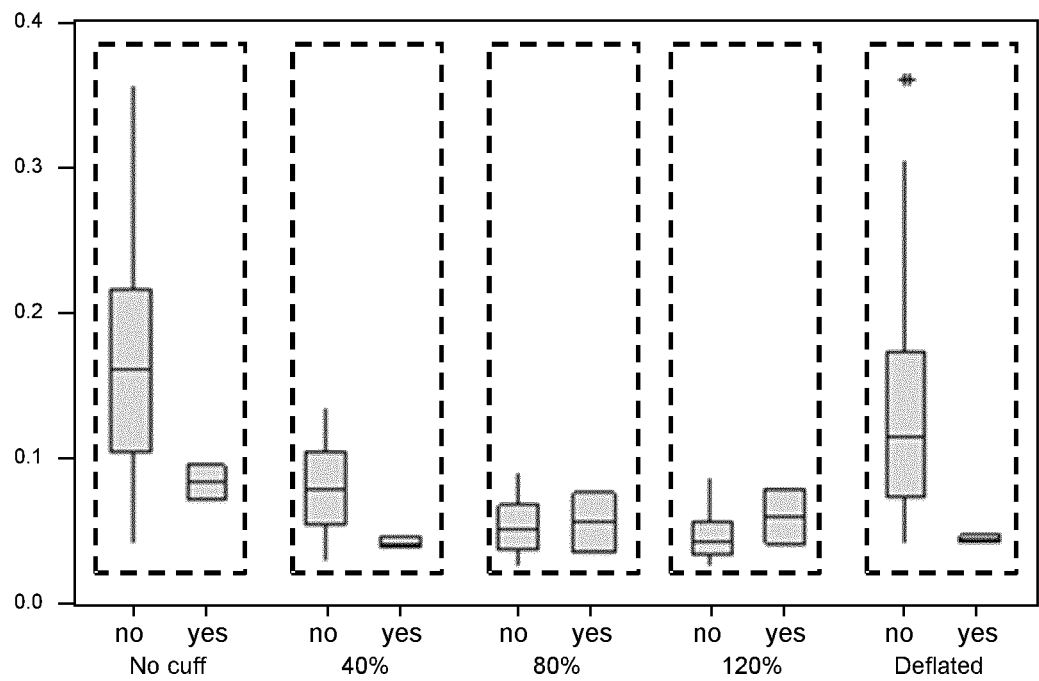
FIG. 12 shows box plots of amplitude levels for no cuff, 40%, 80% and 120% of systolic cuff pressures, and deflated cuff, and divided between patients with ABI above and below 0.9.
Figure 12:
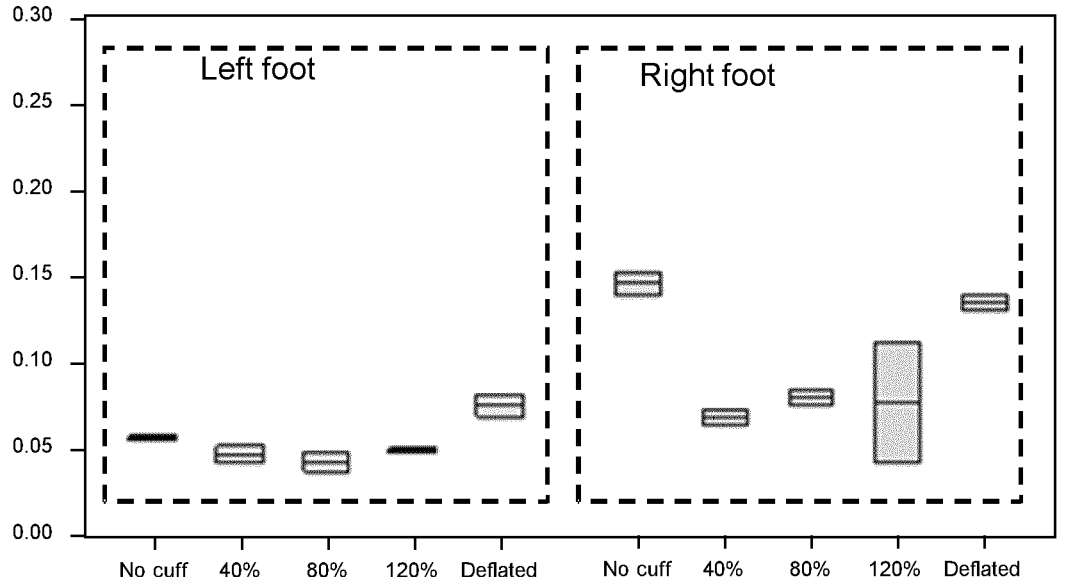

FIG. 12 shows in the top image a box plot of amplitude levels for the no cuff, 40%, 80% and 120% of systolic cuff pressures, and deflated cuff, respectively, and divided between patients with ABI>0.9 (the left plot of each boxed pair of plots) and ABI<(the right plot of each boxed pair of plots). Note that only 2 volunteers showed an ABI of below 0.9 hence the smaller distribution.

The bottom image shows a box plot for the amplitude data acquired of a single volunteer with ABI<0.9 for the no cuff, 40%, 80% and 120% of systolic cuff pressures, and deflated cuff. The left set of plots are for the left foot and the right set of plots are for the right foot, and the subject has a low ABI in the left foot.

The top image shows that on average a low ABI (the plots at the right) indicates a lower signal (particularly in the deflated cuff situation). The bottom image shows that the amplitude signal is also decreased in a region of low ABI compared to a normal region. In the bottom graph, it can be seen that the left foot has a decreased perfusion (the measure for no cuff being lower than for the right foot).

The information above can be used for monitoring the level of perfusion on a subject, for either disease assessment or monitoring (e.g. during a PTA procedure). This is possible by analyzing the PPG signal extracted by averaging the frames from the entire video, a correlation between amplitude of the mono-dimensional PPG signal and the level of perfusion can also be found as shown above. The PPG signal may be mono-dimensional.

The way in which the different measurements explained above may be used to derive a level of perfusion will now be discussed, in particular by combining the information from the amplitude map and the phase map. Optionally, the signal of a reference location (e.g. the hand) may be used in addition to the signal from the region of interest (e.g. the foot).

In a first example, a perfusion index is created dependent on amplitude and phase:

$$\text{Perfusion } (t) = \frac{\text{Median } (A, t)}{\text{Interquartile range } (P, t)} \tag{1}$$

This is a dimensionless indicator rather than an actual measure of perfusion.

The median value is an example of a first value relating to an average of the determined amplitude value for the locations within the region of interest.

The interquartile range is an example of a second value relating to a distribution of the phase values for the locations within the region of interest.

The first and second values are single values for the overall region of interest, and they may be considered to involve a second averaging process (the first averaging process is over time, and the second averaging process is spatial).

Figure 13:
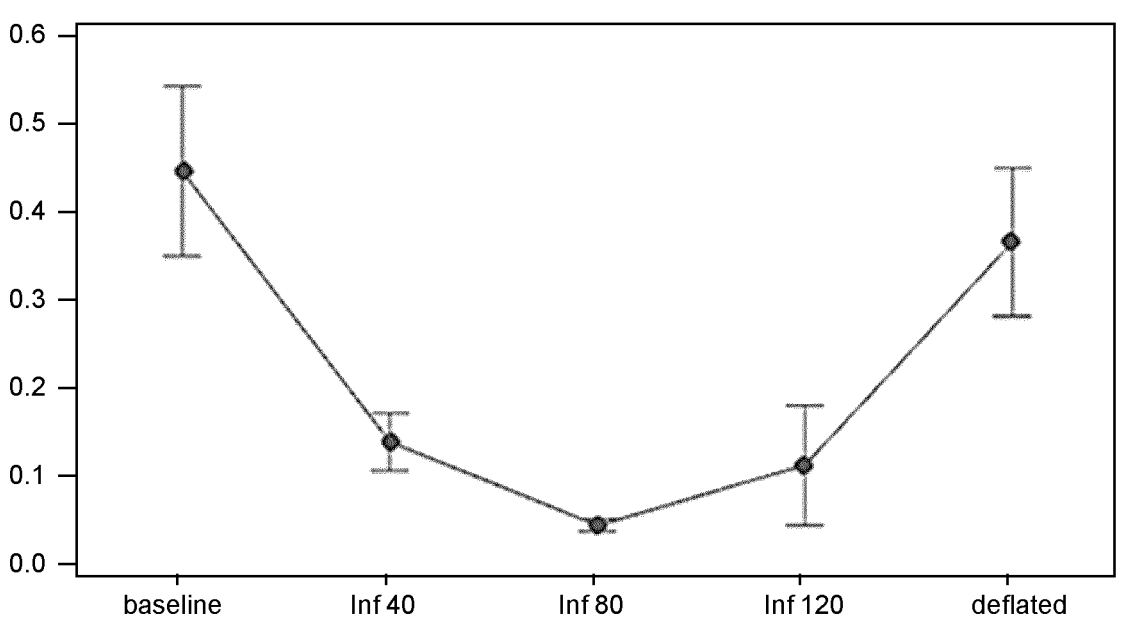
FIG. 13 shows an ANOVA analysis of the median of the amplitude divided by the interquartile range of the phase for no cuff, 40%, 80% and 120% of systolic cuff pressures, and deflated cuff with the 95% confidence interval showing.

FIG. 13 shows an ANOVA analysis of the median of the amplitude divided by the IQR of the phase for the five different cuff pressures.

The perfusion can also be computed using statistical values comparable to the median and IQR. For example, particularly in the case that the distributions are normal, the mean may be used instead of the median, and the standard deviation may be used instead of the inter-quartile range.

If a subject needs to be monitored for a long period of time, another portion of the skin can be used as a reference. This can be useful during PTA or other procedures, since it is also possible to detect a variation in perfusion due to the reopening of one or more vessels.

In this example, the region of interest is for example the sole of the foot, and the reference is taken on the hand (see FIG. 6). The ratio between the perfusion on the foot and the perfusion on the hand may then be computed:

$$\text{Perfusion}_{norm}(t) = \frac{\text{Perfusion}_{Foot}(t)}{\text{Perfusion}_{Hand}(t)} \tag{2}$$

Figure 14:
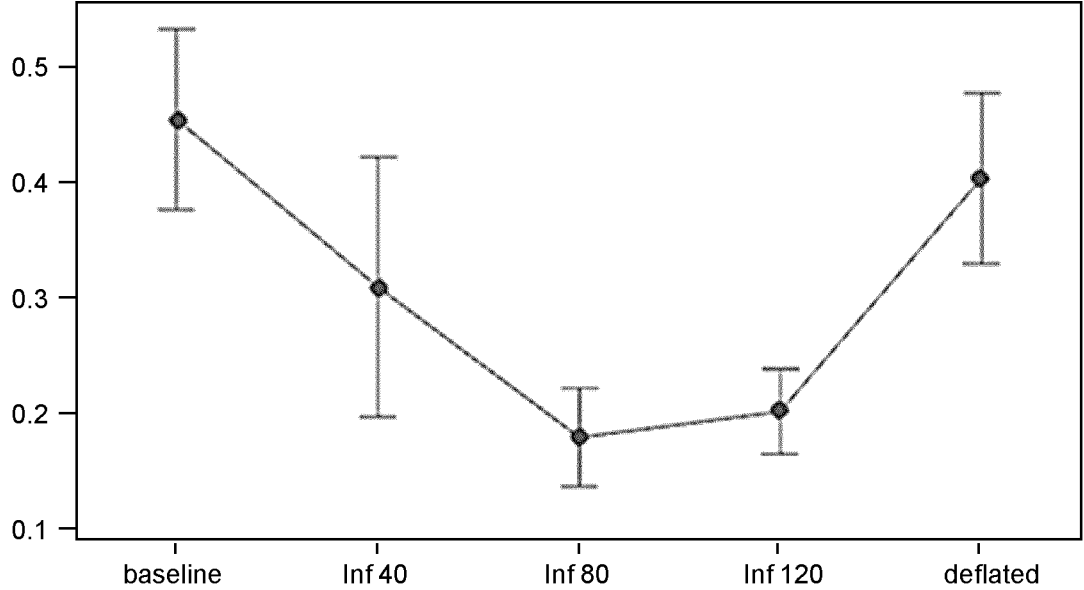
FIG. 14 shows an ANOVA analysis of the median of the amplitude at the foot divided by the median of the amplitude at the hand, for no cuff, 40%, 80% and 120% of systolic cuff pressures, and deflated cuff with the 95% confidence interval showing.

FIG. 14 shows an ANOVA analysis of the median of the amplitude at the foot divided by the median of the amplitude at the hand, for the five different cuff pressures.

The perfusion can be monitored in several ways, for example as a combination of the variables described above. Where perfusion is defined as dependent on the ratio of median to IQR:

$$\text{Perfusion}_{norm}(t) = \frac{\text{Perfusion}_{Foot}(t)}{\text{Perfusion}_{Hand}(t)} = \frac{\dfrac{\text{Median}_{Foot}(A, t)}{\text{Interquartile range}_{Foot}(P, t)}}{\dfrac{\text{Median}_{Hand}(A, t)}{\text{Interquartile range}_{Hand}(P, t)}} \tag{3}$$

Figure 15:
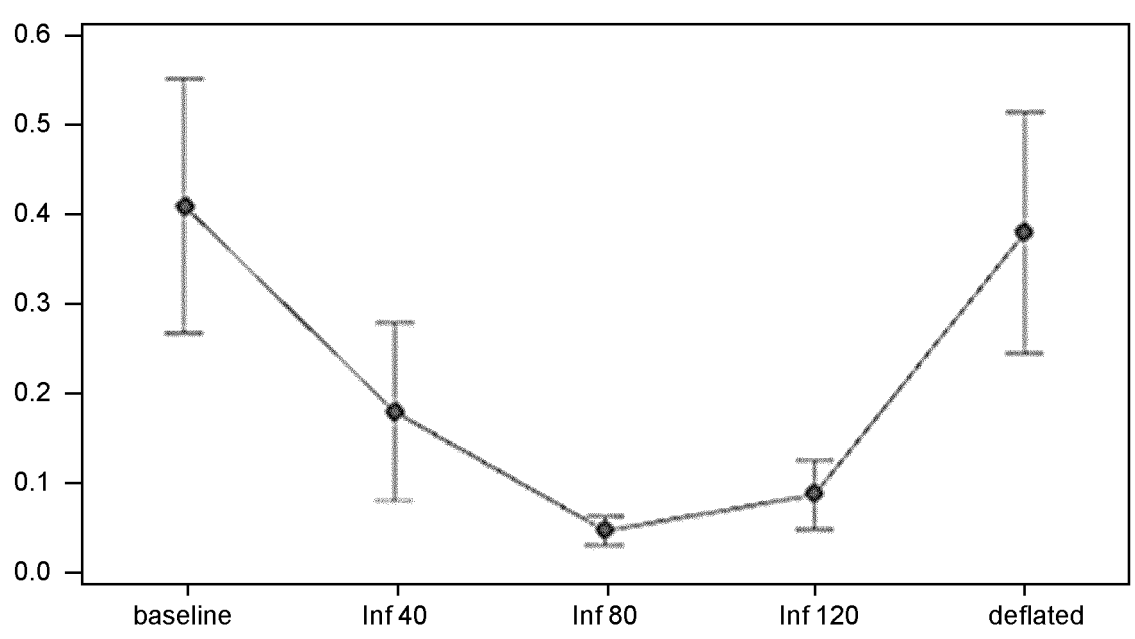
FIG. 15 shows a measurement of the perfusion of the foot, using the perfusion of the hand as a reference, using a first equation with the 95% confidence interval showing.

FIG. 15 shows a measurement of the perfusion of the foot, using the perfusion of the hand as a reference, using equation (3) above.

Another option is the use of the amplitude of mono-dimensional PPG signals extracted from the raw video. The normalized perfusion can be expressed as:

$$\text{Perfusion}_{norm}(t) = \frac{\text{Perfusion}_{Foot}(t)}{\text{Perfusion}_{Hand}(t)} = \frac{1DPPG \text{ signal}_{Foot}(A, t)}{1DPPG \text{ signal}_{Hand}(A, t)} \tag{5}$$

This one dimensional PPG signal (1DPPG) is a single PPG signal computed from the video by averaging all the pixel values.

In this case, there is no phase information. Thus, this simplified implementation of the invention determines the blood perfusion level based on only the amplitudes of the PPG signals, and in particular from a single average of the PPG signals. The index used to represent perfusion in this case may for example be the ratio between the amplitude of the PPG signal at the region of interest (e.g. the foot) and the amplitude of the PPG signal at another region (e.g. the hand).

As mentioned above, body parts remote from the region of interest may be used as reference signals (e.g. the other foot). Alternatively, it is possible to use the value of perfusion acquired at a reference time $t_0$ as a reference:

$$\text{Perfusion}_{norm}(t) = \frac{\text{Perfusion}_{Foot}(t)}{\text{Perfusion}_{Foot}(t_0)} \tag{6}$$

Figure 16:
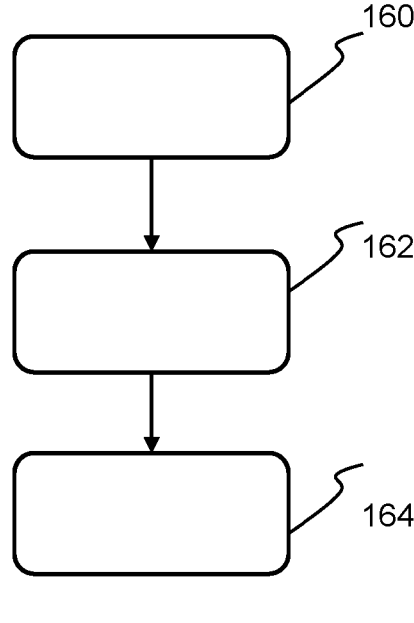
FIG. 16 shows a method of measuring blood perfusion.

FIG. 16 shows a method for monitoring blood perfusion, comprising:

in step 160, acquiring, from at least one sensor, a plurality of photoplethysmography, PPG, signals indicative of light detected in a region of interest of tissue at a plurality of respective locations within the region;

in step 162, processing the acquired plurality of PPG signals to determine an amplitude and a phase of each of the plurality of PPG signals; and in step 164 determining a blood perfusion level at the region of interest based on at least the amplitudes of the PPG signals.

The perfusion level for each location may be obtained in the manner explained above. The region of interest may cover many such locations so a map of perfusion over area may be obtained. A general level of perfusion for the entire region of interest may also be derived, based on a combination (e.g. average) of the perfusion levels of the multiple locations.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

As discussed above, the system makes use of processor to perform the data processing. The processor can be implemented in numerous ways, with software and/or hardware, to perform the various functions required. The processor typically employs one or more microprocessors that may be programmed using software (e.g., microcode) to perform the required functions. The processor may be implemented as a combination of dedicated hardware to perform some functions and one or more programmed microprocessors and associated circuitry to perform other functions.

Examples of circuitry that may be employed in various embodiments of the present disclosure include, but are not limited to, conventional microprocessors, application specific integrated circuits (ASICs), and field-programmable gate arrays (FPGAs).

In various implementations, the processor may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. An apparatus for monitoring blood perfusion, the apparatus comprising a processor configured to:
   acquire, from at least one sensor, a plurality of photoplethysmography, PPG, signals indicative of light detected in a region of interest of tissue at a plurality of respective locations within the region;
   process the acquired plurality of PPG signals to determine an amplitude and a phase of each of the plurality of PPG signals, wherein the phase indicates a relative pulse arrival time to the respective locations; and
   determine a blood perfusion level at the region of interest based on a ratio of a first value indicating the amplitudes of the PPG signals within the region of interest and a second value indicating a measure of distribution of phases of the PPG signals across the region of interest.

2. The apparatus of claim 1, wherein the processor is configured to:
   determine the first value from an average of the determined amplitude value for the locations within the region of interest; and
   determine the second value from a distribution of the phase values for the locations within the region of interest.

3. The apparatus of claim 2, wherein the first value is a median or mean of the amplitudes for the locations.

4. The apparatus of claim 2, wherein the second value is an interquartile range or standard deviation of the phase for the locations.

5. The apparatus of claim 1, wherein the processor is configured to determine the blood perfusion at the region of interest as a value relative to the blood perfusion for the region of interest at a previous time.

6. The apparatus of claim 1, wherein the processor is further configured to:
   acquire from at least one further sensor a plurality of photoplethysmography, PPG, signals, indicative of light detected in a reference region and to determine a blood perfusion level for the reference region; and
   determine the blood perfusion at the region of interest as a value relative to the blood perfusion for the reference region.

7. The apparatus of claim 1, wherein the at least one sensor is a non-contact PPG sensor.

8. A method for monitoring blood perfusion, comprising:
   acquiring, from at least one sensor, a plurality of photoplethysmography, PPG, signals indicative of light detected in a region of interest of tissue at a plurality of respective locations within the region;
   processing the acquired plurality of PPG signals to determine an amplitude and a phase of each of the plurality of PPG signals, wherein the phase indicates a relative pulse arrival time to the respective locations; and
   determining a blood perfusion level at the region of interest based on a ratio of a first value indicating the amplitudes of the PPG signals within the region of interest and a second value indicating a measure of distribution of phases of the PPG signals across the region of interest.

9. The method of claim 8, comprising:
   determining the first value relating to an average of the determined amplitude value for the locations within the region of interest; and
   determining the second value relating to a distribution of the phase values for the locations within the region of interest.

10. The method of claim 9, wherein the first value is a median or men of the amplitudes for the locations and the second value is an interquartile range or standard deviation of the phase for the locations.

11. The method of claim 9, comprising:
   determining the blood perfusion at the region of interest as a value relative to the blood perfusion for the region of interest at a previous time; or
   determining the blood perfusion at the region of interest as a value relative to the blood perfusion for a reference region.

12. A computer program comprising computer program code means which is adapted, when said program is run on a computer of an apparatus for monitoring blood perfusion which includes a PPG sensor, to implement the method of claim 9.

* * * * *